(12) United States Patent
Harvey

(10) Patent No.: US 9,764,997 B1
(45) Date of Patent: Sep. 19, 2017

(54) HIGH DENSITY FUELS FROM RENEWABLE ALCOHOLS

(71) Applicant: The United States of America as represented by the Secretary of the Navy, Washington, DC (US)

(72) Inventor: Benjamin G Harvey, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/099,214

(22) Filed: Apr. 14, 2016

(51) Int. Cl.
| | |
|---|---|
| C07C 5/03 | (2006.01) |
| C07C 2/42 | (2006.01) |
| C07C 5/327 | (2006.01) |
| C10L 1/04 | (2006.01) |
| C07C 2/40 | (2006.01) |
| C07C 1/24 | (2006.01) |
| C07C 1/30 | (2006.01) |
| C07C 1/04 | (2006.01) |

(52) U.S. Cl.
CPC .............. *C07C 5/03* (2013.01); *C07C 1/0485* (2013.01); *C07C 1/24* (2013.01); *C07C 1/30* (2013.01); *C07C 2/403* (2013.01); *C07C 2/42* (2013.01); *C07C 5/327* (2013.01); *C10L 1/04* (2013.01); *C10L 2290/24* (2013.01); *C10L 2290/42* (2013.01)

(58) Field of Classification Search
CPC .. C07C 2/403; C07C 2/42; C07C 5/03; C07C 5/327
See application file for complete search history.

(56) References Cited

U.S. PATENT DOCUMENTS

| | | | |
|---|---|---|---|
| 2,686,209 A * | 8/1954 | Reed ...................... C07C 2/465 585/369 |
| 3,168,581 A | 2/1965 | Pruett | |
| 2011/0245568 A1 | 10/2011 | Khabashesku et al. | |

OTHER PUBLICATIONS

Majumder, S.; Odom, A. L; Tet. Lett. 2008, 49, 1771-1772.
Gotffriedsen, J.; Miioslavina, A.; Edelmann, F. T. Tet. Lett. 2004, 45, 3583-3584.
Osawa, E.; Furusaki, A.; Hashiba, N. et al J. Org. Chem. 1980, 45, 2985-2995.
Jones, W. O. J. Chem. Soc. 1953, 2036; Moore, H. W. J. Am. Chem, Soc. 1964 3398-3399.

* cited by examiner

*Primary Examiner* — Alyssa L Cepluch
(74) *Attorney, Agent, or Firm* — Charlene A. Haley

(57) ABSTRACT

A method for making hydrogenated cyclooctatetraene dimers including cyclo-dimerizing butadiene to form 1,5-cyclooctadiene in the presence of at least one first catalyst, dehydrogenating 1,5-cyclooctadiene to 1,3,5,7-cyclooctatetraene, dimerizing 1,3,5,7-cyclooctatetraene to a $C_{16}$ multicyclic hydrocarbon cyclooctatetraene dimer, and hydrogenating multicyclic hydrocarbon cyclooctatetraene dimer to form hydrogenated cyclooctatetraene dimers.

23 Claims, 1 Drawing Sheet

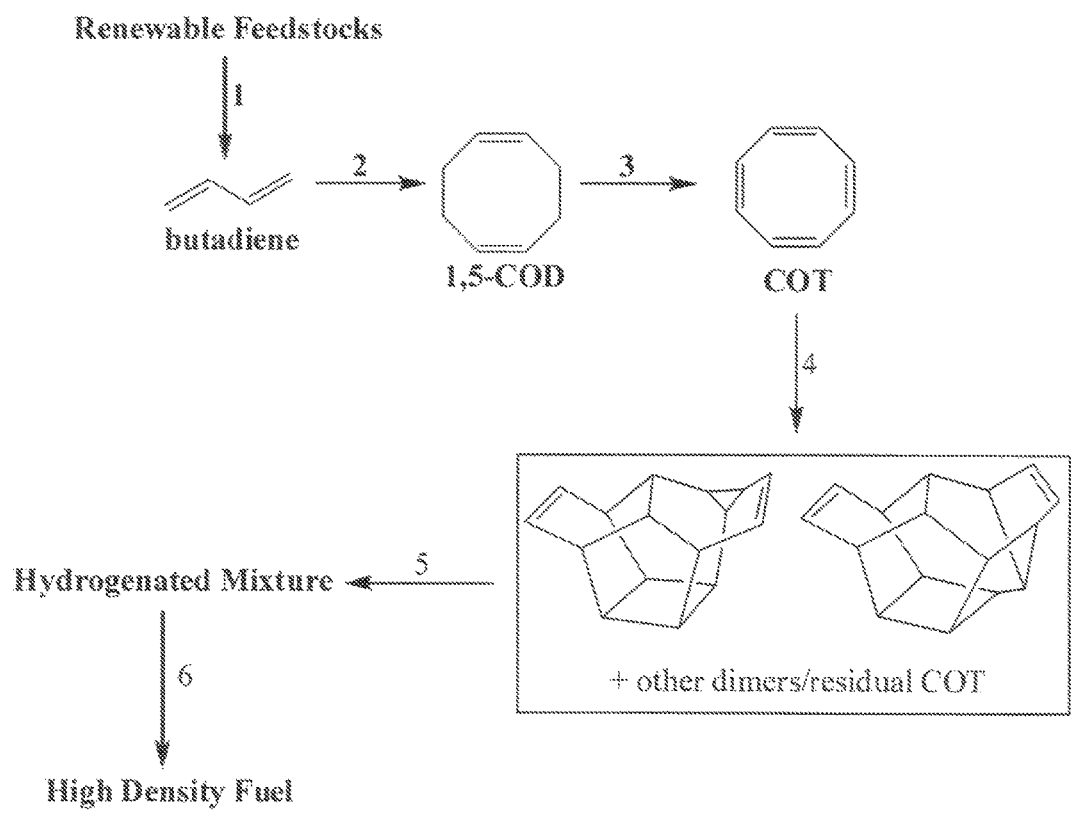

HIGH DENSITY FUELS FROM RENEWABLE ALCOHOLS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to high energy density fuels having applications for the propulsion of volume limited aircraft. The fuels described herein have net heats of combustion ca. 20% higher than JP-10 and can be generated from renewable/sustainable alcohol feedstocks.

BRIEF DESCRIPTION OF THE DRAWING

FIG. 1 is a chemical flow schematic showing the preparation of the cyclooctatetraene (COT) dimer fuels, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to high energy density fuels having applications for the propulsion of volume limited aircraft. The fuels described herein have net heats of combustion ca. 20% higher than JP-10 and can be generated from renewable/sustainable alcohol feedstocks.

Over the last several years, a variety of methods have been developed for the conversion of biomass feedstocks to full-performance renewable fuels. One important pathway relies on the dehydration of renewable alcohols to alkenes followed by oligomerization to jet fuel range hydrocarbons. These alcohol-to-jet (ATJ) processes generate fuels which can be classified as synthetic paraffinic kerosenes (SPKs) and are composed of straight chain or branched paraffins with modest densities (~0.75-0.77 g/mL).

The current invention describes a process for the conversion of renewable alcohols to high performance fuels with densities up to ca. 1.14 g/mL and net heats of combustion of 175,000 btu/gal. For comparison, Navy jet fuel (JP-5) has an NHOC of 125,000 Btu/gal, while JP-10, a high-performance missile fuel, has an NHOC of 141,500 Btu/gal. Thus, the renewable fuels generated by this invention will provide a tactical advantage in addition to reducing the carbon footprint of the Navy.

US patent application 20110245568 A1 describes the dehydrogenation of butene to form butadiene. U.S. Pat. No. 3,168,581 describes the synthesis of 1,5-cyclooctadiene from butadiene with Mn-based catalysts. Majumder, S.; Odom, A. L.; Tet. Lett. 2008, 49, 1771-1772 and Gottfriedsen, J.; Miloslavina, A.; Edelmann, F. T. Tet. Lett. 2004, 45, 3583-3584 describe the synthesis of 1,3,5,7-cyclooctatetraene from 1,5-cyclooctadiene. The thermal dimerization of 1,3,5,7-cyclooctatetraene to multicyclic $C_{16}H_{16}$ hydrocarbons is described in: Osawa, E.; Furusaki, A.; Hashiba, N. et al J. Org. Chem. 1980, 45, 2985-2995; Jones, W. O. J. Chem. Soc. 1953, 2036; Moore, H. W. J. Am. Chem. Soc. 1964 3398-3399.

1. Butadiene is derived from a renewable source.
2. Butadiene is dimerized to 1,5-cyclooctadiene.
3. 1,5-cyclooctadiene is converted to 1,3,5,7-cyclooctatetraene (COT)
4. 1,3,5,7-cyclooctatetraene is dimerized to a C16 multicyclic hydrocarbon (COT-dimer).
5. COT-dimer(s) are hydrogenated to form saturated molecules (HCOT dimers).
6. HCOT dimers are purified to generate a high density fuel.

1. Butadiene is derived from a renewable source. In embodiments butadiene is generated from bio-derived n-butanol by the steps of dehydration to 1-butene followed by dehydrogenation to form butadiene. In embodiments, ethanol is dehydrated to ethylene, dimerized to 1-butene, and then dehydrogenated to form butadiene. In embodiments bio-derived 2,3-butanediol or 1,4-butanediol are dehydrated to form butadiene. In embodiments, butadiene is generated from synthesis gas. Dehydration of n-butanol and ethanol can be accomplished with heterogeneous catalysts including alumina, base-treated alumina, and silylated alumina at temperatures from about 250° C. to 450° C. Selective dehydration of 2,3-butanediol or 1,4-butanediol can be accomplished with heterogeneous catalysts including rare earth metal oxides, particularly scandium oxide ($Sc_2O_3$).

2. Butadiene is dimerized to 1,5-cyclooctadiene in the presence of a catalyst. In embodiments the catalyst includes a transition metal (Mn, Ni, Fe, Co, Pd). In embodiments electron withdrawing ligands are used with Ni catalysts to improve the yield of 1,5-COD over cyclohexane-based products. In embodiments 1,5-COD is separated from the reaction mixture to provide a pure substrate.

3. 1,5-COD is dehydrogenated to form cyclooctatetraene (COT). In embodiments this is accomplished by deprotonating 1,5-COD to generate the dianion $C_8H_8^{(2-)}$. The dianion is then treated with an oxidizing agent to form COT. Alternatively, 1,5-COD can be halogenated followed by dehydrohalogenation with a base to generate COT.

4. COT is thermally dimerized. In embodiments this step is conducted without a solvent. In embodiments a solvent is utilized to produce a preferred distribution. In embodiments a catalyst is utilized to reduce the temperature at which the reaction is conducted.

5. COT dimers are hydrogenated with a heterogeneous or homogenous catalyst based on metals including, but not limited to Ni, Pd, Pt, Ru, Rh, Cu, Cr under a hydrogen pressure. In embodiments, a catalyst is utilized that is selective for hydrogenation of the alkenes present in the structure but not the cyclopropane ring which is present in one of the dimers.

6. The saturated dimer molecules are separated from the catalyst by decantation and purified by distillation to provide a high density fuel. In embodiments the resulting fuel has a density of up to 1.14 g/mL and a volumetric net heat of combustion of up to 175,000 Btu/gal.

Embodiments of the invention generally relate to methods for making hydrogenated cyclooctatetraene dimers including, cyclo-dimerizing butadiene to form 1,5-cyclooctadiene in the presence of at least one first catalyst, dehydrogenating 1,5-cyclooctadiene to 1,3,5,7-cyclooctatetraene, dimerizing 1,3,5,7-cyclooctatetraene to a mixture of $C_{16}$ multicyclic cyclooctatetraene dimers, and hydrogenating multicyclic cyclooctatetraene dimers to form hydrogenated cyclooctatetraene dimers. Another aspect of embodiments of the invention relate to high density fuels and blends produced by the process herein. Yet another aspect of the invention generally relates to hydrogenated cyclooctatetraene dimers produced by the process herein.

Embodiments further include separating the hydrogenated cyclooctatetraene dimers from the first catalyst(s) and purifying the hydrogenated cyclooctatetraene dimers to generate a high density fuel. In embodiments, the butadiene is derived from a renewable source. Embodiments further include dehydrating bio-derived n-butanol to 1-butene followed by dehydrogenation to yield 1,3-butadiene. In embodiments, dehydrogenation of 1,5-cyclooctadiene is accomplished by forming a tetrahalide followed by dehydrohalogenation with a base to yield 1,3,5,7-cyclooctadiene.

Embodiments further include dehydrating ethanol to ethylene, followed by dimerizing ethylene to 1-butene, and dehydrogenation of 1-butene to form butadiene. Embodiments further include dehydrating bio-derived 2,3-butanediol or 1,4-butanediol to form butadiene. Embodiments further include generating the butadiene from synthesis gas. In embodiments, the first catalyst includes a transition metal selected from the group consisting of Mn, Ni, Fe, Co, and Pd. In embodiments, the first catalyst includes nickel and electron withdrawing ligands are used to reduce Diels Alder products and improve the yield of 1,5-cyclooctadiene.

Embodiments further include separating the 1,5-cyclooctadiene from the reaction mixture to provide a pure substrate. In embodiments, dehydrogenating the 1,5-cyclooctadiene to 1,3,5,7-cyclooctatetraene is accomplished by deprotonating 1,5-cyclooctadiene to generate a dianion $C_8H_8(^{2-})$. Embodiments further include treating the dianion with an oxidizing agent to form 1,3,5,7-cyclooctatetraene. In embodiments, dimerizing the 1,3,5,7-cyclooctatetraene to a $C_{16}$ cyclooctatetraene dimer is conducted with a solvent. In embodiments, dimerizing the 1,3,5,7-cyclooctatetraene to $C_{16}$ cyclooctatetraene dimers is conducted with a second catalyst to increase the selectivity of the reaction to dimers and reduce the temperature of the reaction mixture. In embodiments, the cyclooctatetraene dimers are hydrogenated with a heterogeneous or homogenous third catalyst based on metals selected from Ni, Pd, Pt, Ru, Rh, Cu, and Cr under a hydrogen pressure. In embodiments, the second catalyst is a heterogeneous acid catalyst. In embodiments, the dimerizing the 1,3,5,6-cyclooctatetraene is conducted between about 25° C. to about 200° C.

In embodiments, a third catalyst is selective for hydrogenation of the alkenes present in the structure but not the cyclopropane ring which is present in one of the dimers. In embodiments, the high density fuel has a density greater than 1.10 g/mL and a volumetric net heat of combustion greater than 165,000 btu/gal. Embodiments further include mixtures of hydrogenated cyclooctatetraene dimers and exo-tetrahydrodicyclopentadiene (JP-10) in which the hydrogenated cyclooctatetraene dimers include about 10% to about 90% of the blend by volume. Embodiments further include mixtures of hydrogenated cyclooctatetraene dimers and dimethyltetrahydrodicyclopentadiene (RJ-4) in which the hydrogenated cyclooctatetraene dimers having about 10%0 to about 90% of the blend by volume. Embodiments further include mixtures of hydrogenated cyclooctatetraene dimers, hydrogenated norbornadiene dimers (RJ-5), and exo-tetrahydrodicyclopentadiene in which the hydrogenated cyclooctatetraene dimers having about 10% to about 90% of the blend by volume high density fuels.

Prophetic Examples

Prophetic examples are for illustration purposes only and not to be used to limit any of the embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for making a high density fuel, comprising:
    cyclo-dimerizing butadiene in the presence of at least one first catalyst to form 1,5-cyclooctadiene;
    dehydrogenating said 1,5-cyclooctadiene to 1,3,5,7-cyclooctatetraene;
    dimerizing said 1,3,5,7-cyclooctatetraene to a mixture of $C_{16}$ multicyclic cyclooctatetraene dimers;
    hydrogenating said multicyclic hydrocarbon cyclooctatetraene dimers to form a reaction mixture comprising the at least one first catalyst and hydrogenated cyclooctatetraene dimers;
    separating said hydrogenated cyclooctatetraene dimers from the reaction mixture; and
    purifying said separated hydrogenated cyclooctatetraene dimers to generate a high density fuel comprising said hydrogenated cyclooctatetraene dimers, wherein said high density fuel has a density greater than 1.10 g/mL and a volumetric net heat of combustion greater than 165,000 btu/gal.

2. The method according to claim 1, wherein said butadiene is derived from a renewable source.

3. The method according to claim 1, further comprising dehydrating bio-derived n-butanol to 1-butene followed by dehydrogenation to yield said 1,3-butadiene.

4. The method according to claim 1, wherein said dehydrogenating of said 1,5-cyclooctadiene is accomplished by forming a tetrahalide followed by dehydrohalogenation with a base to yield said 1,3,5,7-cyclooctadiene.

5. The method according to claim 1, further comprising dehydrating ethanol to ethylene, followed by dimerizing said ethylene to 1-butene, and dehydrogenating said 1-butene to form said butadiene.

6. The method according to claim 1, further comprising dehydrating bio-derived 2,3-butanediol or 1,4-butanediol to form said butadiene.

7. The method according to claim 1, further comprising generating said butadiene from synthesis gas.

8. The method according to claim 1, wherein said first catalyst includes a transition metal selected from the group consisting of Mn, Ni, Fe, Co, and Pd.

9. The method according to claim 1, wherein said first catalyst includes nickel and electron withdrawing ligands are used to reduce Diels Alder products and improve the yield of 1,5-cyclooctadiene.

10. The method according to claim 1, further comprising separating said 1,5-cyclooctadiene from the reaction mixture to provide a pure substrate.

11. The method according to claim 1, wherein said dehydrogenating of said 1,5-cyclooctadiene to 1,3,5,7-cyclooctatetraene is accomplished by deprotonating 1,5-cyclooctadiene to generate a dianion $C_8H_8^{(2-)}$.

12. The method according to claim 11, further comprising treating said dianion with an oxidizing agent to form said 1,3,5,7-cyclooctatetraene.

13. The method according to claim 1, wherein said dimerizing of said 1,3,5,7-cyclooctatetraene to a $C_{16}$ cyclooctatetraene dimer is conducted with at least one solvent.

14. The method according to claim 1, wherein said dimerizing of said 1,3,5,7-cyclooctatetraene to $C_{16}$ cyclooctatetraene dimers is conducted with a second catalyst to increase the selectivity of the reaction to dimers and reduce the temperature of the reaction mixture.

15. The method according to claim 14, wherein said second catalyst is a heterogeneous acid catalyst.

16. The method according to claim 14, wherein said dimerizing of said 1,3,5,7-cyclooctatetraene is conducted between about 25° C. to about 200° C.

17. The method according to claim 1, wherein said cyclooctatetraene dimers are hydrogenated with a heterogeneous or homogenous third catalyst based on metals selected from the consisting of Ni, Pd, Pt, Ru, Rh, Cu, and Cr under a hydrogen pressure.

18. The method according to claim 15, wherein said third catalyst is selective for hydrogenation of alkenes present in the structure but not a cyclopropane ring which is present in one of the dimers.

19. The method according to claim 1, wherein the high density fuel further comprises exo-tetrahydrodicyclopentadiene, and wherein said hydrogenated cyclooctatetraene dimers comprise about 10% to about 90% of the fuel by volume.

20. The method according to claim 1, wherein the high density fuel further comprises dimethyltetrahydrodicyclopentadiene, and wherein said hydrogenated cyclooctatetraene dimers comprise about 10% to about 90% of the fuel by volume.

21. The method according to claim 1, wherein the high density fuel further comprises hydrogenated norbornadiene dimers and exo-tetrahydrodicyclopentadiene, and wherein said hydrogenated cyclooctatetraene dimers comprise about 10% to about 90% of the fuel by volume.

22. High density fuels produced by the process of claim 1.

23. Hydrogenated cyclooctatetraene dimers produced by the process of claim 1.

* * * * *